United States Patent
Yada et al.

(10) Patent No.: US 7,041,619 B2
(45) Date of Patent: May 9, 2006

(54) PHOSPHONIUM SALTS AND PROCESSES FOR PRODUCTION OF AND USES FOR THE SAME, AND PHOSPHINES DERIVING THE SAME AND PROCESSES FOR PRODUCTION OF THE PHOSPHINES

(75) Inventors: Kazuyuki Yada, Kamisu-machi (JP); Kenji Shimoyamada, Kamisu-machi (JP); Masahiro Muranaka, Kamisu-machi (JP); Junichi Fuji, Kamisu-machi (JP); Shigeaki Suzuki, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/895,852

(22) Filed: Jul. 22, 2004

(65) Prior Publication Data

US 2004/0260118 A1 Dec. 23, 2004

Related U.S. Application Data

(62) Division of application No. 10/109,876, filed on Apr. 1, 2002, now Pat. No. 6,790,985.

(30) Foreign Application Priority Data

| Apr. 13, 2001 | (JP) | 2001/114942 |
| Apr. 13, 2001 | (JP) | 2001/114943 |
| Sep. 28, 2001 | (JP) | 2001/302354 |

(51) Int. Cl.
*B01J 31/00* (2006.01)

(52) U.S. Cl. .................. 502/164; 502/213; 562/35; 562/30

(58) Field of Classification Search ................ 502/164, 502/213; 208/208; 562/35, 30

See application file for complete search history.

(56) References Cited

U.S. PATENT DOCUMENTS

| 4,142,060 A | 2/1979 | Kuntz |
| 4,390,476 A | 6/1983 | Marky |
| 4,483,802 A | 11/1984 | Gartner et al. |
| 4,623,490 A | 11/1986 | Bexten et al. |
| 4,710,321 A | 12/1987 | Bahrmann et al. |
| 4,716,250 A | 12/1987 | Abatjoglou et al. |
| 4,927,960 A * | 5/1990 | Maeda et al. ............... 562/512 |
| 4,965,404 A | 10/1990 | Maeda et al. |
| 5,100,854 A * | 3/1992 | Maeda et al. ............... 502/164 |
| 5,481,049 A | 1/1996 | Sato et al. |
| 5,556,849 A | 9/1996 | Abrams et al. |

OTHER PUBLICATIONS

CA:122:213604 abs of JP 06321828 Nov. 1994.

* cited by examiner

*Primary Examiner*—Chukwuma Nwaonicha
(74) *Attorney, Agent, or Firm*—Oblon, Spivak, McClelland, Maier & Neustadt, P.C.

(57) ABSTRACT

Phosphonium salts represented by the general formula (I)

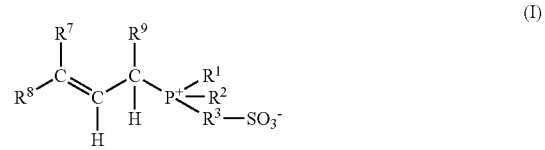

wherein $R^1$ and $R^2$ each represents a phenyl group which may be substituted by a lower alkyl group, $R^3$ represents a phenylene group which may be substituted by a lower alkyl group, $R^7$ and $R^8$ each represents a hydrogen atom or a hydrocarbon group having 1 to 12 carbon atoms which may be substituted and $R^9$ represents a hydrogen atom or a hydrocarbon group having 1 to 5 carbon atoms which may be substituted; processes for producing the same and uses for the same; phosphines providing the same, and processes for producing said phosphines.

14 Claims, No Drawings

PHOSPHONIUM SALTS AND PROCESSES FOR PRODUCTION OF AND USES FOR THE SAME, AND PHOSPHINES DERIVING THE SAME AND PROCESSES FOR PRODUCTION OF THE PHOSPHINES

This is a divisional application of application Ser. No. 10/109,876, now allowed, filed on Apr. 1, 2002.

BACKGROUND OF THE INVENTION

1. Field of the Invention

The present invention relates to phosphonium salts and processes for production of and uses for the same and, further, to phosphines deriving the same and processes for producing said phosphines.

The phosphonium salts provided by the present invention are useful as components of catalysts accelerating telomerization of a conjugated diene and an active hydrogen compound. Accordingly, the above uses include telomerization catalysts comprising the phosphonium salts provided by the present invention and, also, processes with use of the telomerization catalysts for producing alkadienyl compounds. The alkadienyl compounds obtained by the telomerization, such as 2,7-octadien-1-ol, 1,7-octadien-3-ol, 1-acetoxy-2,7-octadiene and 1-amino-2,7-octadiene are usable, for example, as starting materials for various polymers, medicines, agricultural chemicals and the like.

2. Description of the Related Art

U.S. Pat. No. 4,142,060 and GB1553002 disclose telomerization of dienes in the presence of a catalyst comprising a water-soluble phosphine and a palladium compound. Known water-soluble phosphines include the quaternary ammonium salts of (sulfophenyl)diphenylphosphine, di(sulfophenyl)phenylphosphine or tri(sulfophenyl)phosphine. Of these phosphines, the tetraethylammonium salt of tri(3-sulfophenyl)phosphine containing 60% of trivalent phosphorus is actually used for telomerization of butadiene. Such a tetraethylammonium salt of tri(3-sulfophenyl)phosphine contains an impurity of pentavalent phosphorus. According to a study by the present inventors, use of a phosphine containing a large amount of an impurity of pentavalent phosphorus, as a constituent of a telomerization catalyst, leads to accumulation of impurities in the reaction mixture, thereby changing the solubility of the reaction substrates and exerting similar bad influences on the reaction.

"Applied Catalysis A: General", 131(1995) 167–178 describes use of the dimethyldodecylamine salt of diphenylphosphinobenzene-3-monosulfonic acid (water-insoluble), which has a surface-active property, for telomerization of butadiene. However, this reaction has a low rate.

U.S. Pat. No. 4,716,250 and EP0254937B1 disclose the higher amine salts, such as trioctylammonium salt, dimethyloctylammonium salt and dimethyldodecylammonium salt, of diphenylphosphinobenzene-3-sulfonic acid as ligands for hydroformylation catalysts. U.S. Pat. No. 5,663,426 and EP0704450B1 disclose sulfonated phosphines as constituents of water-soluble catalyst systems for C—C bond forming reactions such as hydroformylation. These patents describe, concretely, the steps of sulfonating a phosphine in a mixed liquid comprising fuming sulfuric acid, boric acid and concentrated sulfuric acid, treating the sulfonated product with a solution of triisooctylamine in toluene, to obtain the triisooctylamine salt of the sulfonated phosphine, introducing the salt into an organic phase, and subjecting the resulting organic phase to extraction with an aqueous sodium hydroxide solution, to obtain the sodium salt of the sulfonated phoshine. These higher amine salts of sulfonated phosfines are insoluble in water and hence cannot provide commercially advantageous telomerization catalysts.

It is known, generally, with catalysts comprising a phosphine and a transition metal, that while a large amount of the phosphine realizes good stability of the resulting catalyst, which has, however, an insufficient catalytic activity, a small amount of the phosphine leads to poor stability of the catalyst, which cannot exert the catalytic activity continuously. The catalytic activity and the stability are thus incompatible with each other, which renders it impossible, with use of a catalyst comprising a phosphine, to produce alkadienyl compound commercially advantageously.

In order to solve the above problems, Japanese Patent No. 2635519, U.S. Pat. No. 4,927,960, U.S. Pat. No. 4,992,609, U.S. Pat. No. 5,100,854 and EP0296550B1 disclose a process for carrying out telomerization with use of a catalyst comprising a phosphonium salt and a palladium compound. For instance, telomerization of a conjugated alkadiene and water is carried out with use of a catalyst comprising a water-soluble phosphonium salt containing a group of the formula —$SO_3M$ or —COOM (wherein M represents an alkali metal such as lithium, potassium or sodium) and a palladium compound, in the presence of a mixed solvent of sulfolane and water and under a pressure of carbon dioxide.

The present inventors made a test run of dimerization of butadiene and water with use of a telomerization catalyst comprising a phosphonium salt derived from an alkali metal salt of diphenylphosphinobenzene-3-monosulfonic acid and a palladium compound, continuously over a long period of time, to find occasional formation of precipitates in the reaction zone, which caused clogging of the piping and decreased the heat conduction efficiency of the reactor.

As a result of an intensive study to clarify the mechanism involved in the precipitation, the present inventors have found that, on dimerizing butadiene and water continuously over a long period of time, the concentration of the alkali metal ion constituting the phosphonium salt in the reaction mixture increases to an unexpected level, that the alkali metal ion reacts with a reaction accelerator of hydrogencarbonate ion or carbonate ion to form the alkali metal hydrogencarbonate and/or alkali metal carbonate, which precipitates in the reaction mixture. These phenomena were quite unexpected, because, originally, alkali metal hydrogencarbonates and alkali metal carbonates maintain the state of solution under the conditions of dimerization of butadiene and water.

SUMMARY OF THE INVENTION

Accordingly, an object of the present invention is to provide a phosphonium salt constituting a telomerization catalyst which, on telomerizing a conjugated diene and an active hydrogen compound on a commercial scale for a long period of time, will not cause any precipitation at all in the reaction mixture.

A further object of the present invention is to provide a process for producing the above phosphonium salt.

A still further object of the present invention is to provide a telomerization catalyst comprising the above phosphonium salt.

Another object of the present invention is to provide a process for producing an alkadienyl compound from a conjugated diene and an active hydrogen compound with use of the above telomerization catalyst.

Still another object of the present invention is to provide an amine salt of a sulfonated phosphine which is usable as a starting material for the above telomerization catalyst.

Yet another object of the present invention is to provide a process for producing with ease the above amine salt of the sulfonated phosphine having a high purity.

The present invention, in one aspect thereof, provides a phosphonium salt represented by the general formula (I) (hereinafter referred to as "phosphonium salt (I)")

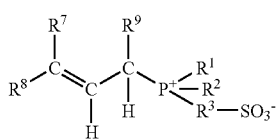
(I)

wherein $R^1$ and $R^2$ each represents a phenyl group which may be substituted by a lower alkyl group, $R^3$ represents a phenylene group which may be substituted by a lower alkyl group, $R^7$ and $R^8$ each represents a hydrogen atom or a hydrocarbon group having 1 to 12 carbon atoms which may be substituted and $R^9$ represents a hydrogen atom or a hydrocarbon group having 1 to 5 carbon atoms which may be substituted.

In another aspect, the present invention provides a process for producing the phosphonium salt (I), which comprises reacting an alkenyl compound represented by the general formula (II) (hereinafter referred to as "alkenyl compound (II)")

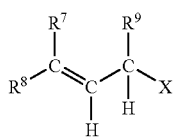
(II)

wherein $R^7$, $R^8$ and $R^9$ are as defined above, X represents a hydroxy group, an alkoxy group, an alkenyloxy group, an acyloxy group, a hydroxycarbonyloxy group, alkoxycarbonyloxy group or a phenoxy group which may be substituted, and an amine salt of a sulfonated phosphine represented by the general formula (III) (hereinafter referred to as "phosphine compound (III)")

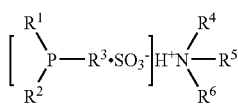
(III)

wherein $R^1$, $R^2$ and $R^3$ are as defined above and $R^4$, $R^1$ and $R^6$ each represents a lower alkyl group, in the presence of a palladium compound.

In a third aspect, the present invention provides a telomerization catalyst (hereinafter referred to as "telomerization catalyst (I)") comprising a phosphonium salt (I) and a palladium compound but comprising no alkali metal compound.

In a fourth aspect, the present invention provides a process for producing an alkadienyl compound: which comprises reacting a conjugated diene with an active hydrogen compound in the presence of a catalyst, characterized in that the telomerization catalyst (I) is used as the catalyst.

In a fifth aspect, the present invention provides the phosphine compound (III).

In a sixth aspect, the present invention provides a process for producing the phosphine compound (III), which comprises reacting a sulfonic acid represented by the general formula (IV-1) (hereinafter referred to as "sulfonic acid (IV-1)")

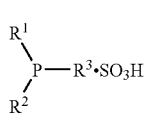
(IV-1)

wherein $R^1$, $R^2$ and $R^3$ are as defined above, and an amine represented by the general formula (V) (hereinafter referred to as "amine (V)")

$$R^4R^5R^6N \qquad (V)$$

wherein $R^4$, $R^5$ and $R^6$ are as defined above, in an acyclic ketone having 6 to 9 carbon atoms.

In a seventh aspect, the present invention provides a process for producing the phosphine compound (III), which comprises reacting a sulfonic acid alkali metal salt represented by the general formula (IV-2) (hereinafter referred to as "alkali metal sulfonate (IV-2)")

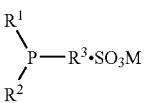
(IV-2)

wherein $R^1$, $R^2$ and $R^3$ are as defined above and M represents an alkali metal, and the amine (V) in the presence of carbon dioxide and water.

DETAILED DESCRIPTION OF THE INVENTION

In the above general formulas, the lower alkyl group which may be possessed by the phenyl group represented by $R^1$ or $R^2$, or by the phenylene group represented by $R^3$, and the lower alkyl group represented by $R^4$, $R^5$ or $R^6$ include those capable of forming phosphine compounds (III) that are water-soluble. Preferred examples of the lower alkyl group are those having 1 to 4 carbon atoms, e.g. methyl, ethyl, propyl and butyl. Of these, methyl group and ethyl group are more preferred. Examples of the hydrocarbon groups having 1 to 12 carbon atoms which may be represented by $R^7$ or $R^8$ are aliphatic hydrocarbon groups such as alkyl groups, e.g. methyl, ethyl, n-propyl, n-butyl, n-pentyl and n-octyl, and alkenyl groups, e.g. 2-propenyl, 3-butenyl and 4-pentenyl; alicyclic hydrocarbon groups, such as cycloalkyl groups, e.g. cyclohexyl; and aromatic hydrocarbon groups, such as aryl groups, e.g. phenyl and tolyl, and aralkyl groups, e.g. benzyl. Examples of the hydrocarbon group having 1 to 5 carbon atoms which may be represented by $R^9$ are aliphatic hydrocarbon groups such as alkyl groups, e.g. methyl, ethyl and propyl, and alkenyl groups, e.g. allyl and 4-pentenyl.

Examples of the alkoxy group which may be represented by X are methoxy, ethoxy, propoxy and butoxy; those of the alkenyloxy group are propenyloxy, butenyloxy, allyloxy and 2,7-octadienyloxy; those of the acyloxy group are formyloxy, acetyloxy and propionyloxy; and those of the alkoxycarbonyloxy group are methoxycarbonyloxy and butoxycarbonyloxy. Examples of the substituent which may be possessed by the phenyl group that may be represented by X are alkyl groups, e.g. methyl and ethyl and alkyloxy groups, e.g. methoxy and ethoxy. Examples of the alkali metal represented by M are lithium, potassium and sodium.

The phosphonium salts (I) are novel compounds that have not been described in the literature. These salt are markedly soluble in the telomerization reaction mixture and yield an excellent reaction result when used as a constituent of telomerization catalysts. Furthermore, these salts contain no alkali metal, so that no precipitates of alkali metal salts form in the reaction mixture. Preferred examples of the phosphonium salts (I) are those represented by the general formula (I) wherein $R^7$ and $R^8$ are each a hydrogen atom or an aliphatic hydrocarbon group having 1 to 12 carbon atoms and $R^9$ is a hydrogen atom or an aliphatic hydrocarbon group having 1 to 5 carbon atoms, as well as those represented by the general formula (I) wherein $R^1$ and $R^2$ are each a phenyl group or a phenyl group having a methyl group or ethyl group, and $R^3$ is a 1,3-phenylene group or a 1,3-phenylene group having a methyl group or ethyl group. Of these, phosphonium salts (I) with $R^1$ and $R^2$ each being a phenyl group or 2-methylphenyl group and $R^3$ being a 1,3-phenylene group or 4-methyl-1,3-phenylene group are preferred.

The process for producing phosphonium salts (I) is now described.

Examples of the alkenyl compound (II) used are allyl-type alcohols, e.g. allyl alcohol, 1-methyl-2-propen-1-ol, 2-buten-1-ol, 2,5-hexadien-1-ol, 2,7-octadien-1-ol, 1,4-pentadien-3-ol and 1,7-octadien-3-ol; allyl-type ethers, e.g. allyl ethyl ether, diallyl ether, methyl 2,7-octadienyl ether, di(2,7-octadienyl) ether and allyl phenyl ether; and allyl-type esters, e.g. allyl acetate, 2,5-hexadienyl acetate, 2,7-octadienyl acetate, 1-vinyl-5-hexenyl acetate and 2-octenyl propionate.

The phosphine compounds (III) are novel compounds that have not been described in the literature. The phosphine compounds (III) are water-soluble and markedly soluble in solutions for preparing telomerization catalysts. Preferred examples of the phosphine compounds (III) are amine salts of sulfonated phosphines represented by the general formula (III) wherein $R^1$ and $R^2$ are each a phenyl group or a phenyl group having a methyl group or ethyl group, $R^3$ is a 1,3-phenylene group or a 1,3-phenylene group having a methyl group or ethyl group, and $R^4$, $R^5$ and $R^6$ are each a methyl group or ethyl group. Of these, amine salts of sulfonated phosphines with $R^1$ and $R^2$ each being a phenyl group or 2-methylphenyl group, $R^3$ being a 1,3-phenylene group or 4-methyl-1,3-phenylene group, and $R^4$, $R^5$ and $R^6$ being each a methyl group or an ethyl group are preferred. Concrete examples of the phosphine compounds (III) are triethylammonium 3-(diphenylphosphino)benzenesulfonate, trimethylammonium 3-(diphenylphosphino)benzenesulfonate and triethylammonium 3-(bis(2-methylphenyl)phosphino)-4-methylbenzenesulfonate.

The alkenyl compound (II) is used in an amount of preferably at least one molar equivalent, more preferably 1 to 10 molar equivalents, relative to the phosphine compound (III) used.

Examples of the palladium compound used on production of the phosphonium salt (I) are palladium (II) compounds, e.g. palladium acetylacetonate, π-allylpalladium acetate, palladium acetate, palladium carbonate, palladium chloride and bisbenzonitrile-palladium chloride; and palladium (0) compounds, e.g. bis(1,5-cyclooctadiene)palladium and tris(dibenzylideneacetone)dipalladium. Where a palladium (II) compound is used, a reducing agent may be used in combination to reduce palladium (II) to palladium (0). Examples of the reducing agent are alkali metal hydroxides such as sodium hydroxide, formic acid, sodium phenolate, sodium borohydride, hydrazine, zinc powder and magnesium. The reducing agent is used in an amount preferably ranging from the stoichiometric amount required for the reduction to 10 times the amount. The palladium compound is used in an amount preferably such that the concentration of palladium atom in one liter of the reaction mixture will become 0.1 to 10 milligram atoms, more preferably 0.5 to 5 milligram atoms.

On preparation of the phosphonium salt (I), water containing carbonate ion and/or hydrogen carbonate ion may be permitted to be present in the reaction zone in order to accelerate the reaction. In practice, it is recommended to derive the carbonate ion and/or hydrogen carbonate ion in the reaction zone from carbon dioxide, a hydrogencarbonate such as sodium hydrogencarbonate or a carbonate such as sodium carbonate. It is particularly desirable to derive the ion from, among the above, carbon dioxide, which prevents contamination of alkali metal salts. Where carbon dioxide is used for this purpose, there may be added a tertiary amine or quaternary ammonium ion in order to increase the carbonate ion concentration in the reaction zone. Where carbon dioxide is used, its partial pressure is generally 0 to 4.9 MPa (atmospheric pressure to 50 atm) (gauge pressure) and preferably 0 to 0.98 MPa (atmospheric pressure to 10 atm)(gauge pressure) in practice. Where a tertiary amine or quaternary ammonium ion is present in the reaction zone, the phosphonium salt (I) is considered to be in equilibrium with a phosphonium salt represented by the general formula (IX)

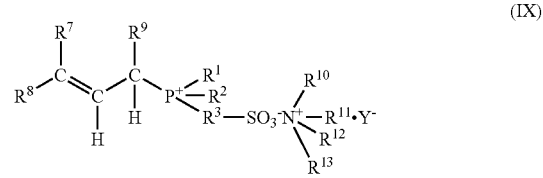

wherein $R^1$, $R^2$, $R^3$, $R^7$, $R^8$ and $R^9$ are as defined above, $R^{10}$ represents a hydrogen atom or a hydrocarbon group, $R^{11}$, $R^{12}$ and $R^{13}$ each represents a hydrocarbon group and Y represents a hydroxy group, an alkoxy group, an alkenyloxy group, an acyloxy group, a hydroxycarbonyloxy group, an alkoxycarbonyloxy group or a phenoxy group which may be substituted.

The preparation of the phosphonium salts (I) can be carried out in the presence of an organic solvent which is inert to the reaction and capable of dissolving the alkenyl compound (II) and phosphine compound (III). Examples of the organic solvent are ethers, e.g. diethyl ether, tetrahydrofuran, dioxane and ethylene glycol dimethyl ether; secondary and tertiary alcohols, e.g. t-butyl alcohol and isopropyl alcohol; ketones, e.g. acetone and methyl isobutyl ketone; nitriles, e.g. acetonitrile and benzonitrile; amides, e.g. acetamide and N,N-dimethylformamide; sulfoxides, e.g. dimethyl sulfoxide; sulfones, e.g. sulfolane; carboxylic acids, e.g. acetic acid and propionic acid; esters, e.g. ethyl acetate and methyl benzoate; aromatic hydrocarbons, e.g. benzene and toluene; and cyclic and acyclic aliphatic hydrocarbons, e.g. hexane and cyclohexane. These organic solvents are generally used alone, but may also be used in combination.

The phosphonium salt (I) is prepared generally at a temperature in a range of 10 to 80° C. The atmosphere of the reaction zone is preferably a gaseous atmosphere such as carbon dioxide or nitrogen which does not impair the reaction efficiency. These gases may be used either singly or in combination.

The phosphonium salt (I) thus obtained can be separated from the reaction mixture and purified, for example as follows. The reaction solvent used, unreacted alkenyl compound (II) and the like are distilled off from the reaction mixture under a reduced pressure. The resulting residue is washed with a solvent that does not dissolve the phosphonium salt (I), to remove the palladium compound used, and the desired phosphonium salt (I) is obtained.

In combination with the above palladium compounds, the phosphonium salts (I) give the telomerization catalysts (I) of the present invention. The telomerization catalysts (I) contain no alkali metals, thereby forming no alkali metal hydrogencarbonate or alkali metal carbonate that would form the above precipitates, even when the telomerization reaction liquid contains hydrogencarbonate ion or carbonate ion. The mixture obtained by reacting an alkenyl compound (II) and a phosphine compound (III) in the presence of a palladium catalyst contains the corresponding phosphonium salt (I) and the palladium compound and hence can be used as it is as a telomerization catalyst (I) Or, the mixture may be subjected to distillation under a reduced pressure to remove the reaction solvent, unreacted alkenyl compound (II) and the like, and the resulting residue is used as a telomerization catalyst (I).

The concentration of the phosphonium salt (I) in the telomerization catalyst (I) can vary over a wide range, but is preferably at least 2 moles, more preferably 4 to 50 moles, per gram-atom of palladium contained in the palladium compound used. The telomerization catalyst (I) may be added to the telomerization reaction zone either by adding a phosphonium salt (I) and a palladium compound separately or by adding a mixture of the two.

Next, the process for producing alkadienyl compounds which comprises reacting a conjugated diene and an active hydrogen compound in the presence of a telomerization catalyst (I) is described.

Examples of the conjugated diene are butadiene and isoprene. The active hydrogen compound includes compounds having in the molecules thereof at least one active hydrogen atom. Examples of such compounds are water, alcohols, phenols, ammonia, amines and carboxylic acids. Concrete examples of the alcohols are methanol, ethanol, butanol, allyl alcohol, 2-ethylhexanol, octadienol, stearyl alcohol, diethylene glycol, neopentyl glycol, pentaerythritol, trimethylolpropane and polyethylene glycol. Examples of the phenols are phenol, cresol and t-butylphenol. Examples of amines are methylamine, dimethylamine, ethylamine, diethylamine, butylamine, morpholine and piperazine. Examples of the carboxylic acids are formic acid, acetic acid, propionic acid, adipic acid, benzoic acid and phthalic acid. As the active hydrogen compound, it is desirable to use water, an alcohol or a carboxylic acid. The amounts of the conjugated diene and active hydrogen compound used are, varying depending on the types of the compounds used and the intended products though, preferably in a range of 0.3 to 20 moles of the active hydrogen compound based on one mole of the conjugated diene.

Additives may be used for the telomerization, in order to increase the reaction rate. Examples of usable additives are bases such as aliphatic tertiary amines, e.g. trimethylamine and triethylamine; salts of these bases with acids such as carbonic acid, phosphoric acid, acetic acid, boric acid and methanesulfonic acid; and weak acids, such as boric acid, phosphorous acid and phenol. Where water is used as the active hydrogen compound, it is desirable to use as an additive the carbonate or hydrogencarbonate of an aliphatic tertiary amine.

Where no tertiary amine or quaternary ammonium ion is present in the reaction zone, the phosphonium salt (I) constituting the telomerization catalyst (I) is present as it is. On the other hand, where a tertiary amine or quaternary ammonium ion is present in the reaction zone, the phosphonium salt (I) is considered to be in equilibrium with a phosphonium salt represented by the general formula (X).

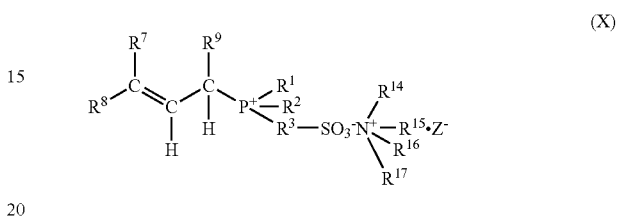

wherein $R^1$, $R^2$, $R^3$, $R^7$, $R^8$ and $R^9$ are as defined above, $R^{14}$ represents a hydrogen atom or a hydrocarbon group, $R^{15}$, $R^{16}$ and $R^{17}$ each represents a hydrocarbon group and Z represents a hydroxy group, an alkoxy group, an alkenyloxy group, an acyloxy group, a hydroxycarbonyloxy group, an alkoxycarbonyloxy group or a phenoxy group which may be substituted.

The telomerization can be carried out by permitting the active hydrogen compound used to act as a solvent for the reaction. However, it is desirable to effect the telomerization in the presence of an independent organic solvent which does not affect the reaction badly. Where water is used as the active hydrogen compound, it is preferred to use an organic solvent of sulfolane, dimethyl sulfoxide or the like, in particular sulfolane in view of the reaction rate.

The telomerization is carried out preferably at a temperature in a range of 40 to 100° C., more preferably in a range of 60 to 80° C. On effecting hydrodimerization with use of water as the active hydrogen compound, the reaction is desirably carried out in the presence of carbon dioxide. In this case, any carbon dioxide that will be present as carbon dioxide in the reaction zone can be used, and its examples include molecular carbon dioxide, carbonic acid, carbonates or hydrogencarbonates. Where one wishes to use molecular carbon dioxide, it is possible to carry out the reaction under a pressure of carbon dioxide, in order to increase the solubility of molecular carbon dioxide in the reaction liquid. The reaction pressure can be selected from a range between 0 to 9.8 MPa (atmospheric pressure to 100 kg/cm²) (gauge pressure) which includes the vapor pressures of the conjugated diene, the reaction product and solvent at the reaction temperature. On this occasion, an inert gas such as nitrogen or argon can be present in combination. Although the reaction may be carried out batch-wise, it is desirable to employ a continuous process for commercial production.

The telomerization catalyst (I) comprising a phosphonium salt (I) and a palladium compound is, after completion of the telomerization, separated and recovered from the reaction mixture by distillation, extraction or like methods. On this occasion, extraction is preferably employed, which insures little deterioration of the catalytic activity and a long-period circulative use of the catalyst components. The extraction may be performed by, for example, subjecting the reaction mixture after completion of the telomerization to extraction with an extracting agent of a solvent that will not mix with the reaction solvent used. Since the telomerization catalysts (I) of the present invention have a high water-solubility, use of a reaction solvent comprising water permits the catalyst components to be separated easily. The thus separated catalyst components can be returned as they are to the reaction zone and thus circulatively used, which procedure suppresses loss of the catalyst components.

Next, the process for producing phosphine compounds (III) from sulfonic acids (IV-1) is described.

The reaction of a sulfonic acid (IV-1) and an amine (V) is performed in a solvent of an acyclic ketone having 6 to 9 carbon atoms. Examples of the acyclic ketone are 4-methyl-2-pentanone, 5-methyl-3-heptanone, 2-octanone, 3-octanone and 5-nonanone. These acyclic ketones may be used either singly or in combination of 2 or more. Of the above ketones, 4-methyl-2-pentanone is desirably used. The solvent is used in such an amount as to dissolve sufficiently the sulfonic acid (IV-1) used. Excessive use being economically inefficient, the amount is preferably 2 to 10 ml based on 1 g of the sulfonic acid (IV-1), more preferably 3 to 6 ml on the same basis.

With the above reaction, the amine (V) is used preferably in an amount of 1.0 to 10.0 moles based on 1 mole of the sulfonic acid (IV-1), more preferably in an amount of 1.0 to 2.0 moles on the same basis. In order to suppress by production of phosphine oxide which is one of impurities to be contained in the product phosphine (III), the reaction is desirably carried out, over the whole process, under an atmosphere of an inert gas such as nitrogen, argon or mixtures thereof and excluding oxygen. The reaction temperature is desirably in a range of 0 to 60° C., more preferably in a range of 10 to 30° C. If the reaction temperature exceeds 60° C., phosphine oxide will tend to form easily, which is not preferred. The reaction may be permitted to proceed very long, but the reaction time is desirably in a range of 0.25 to 3 hours in view of efficiency.

The thus obtained phosphine compound (III) can be separated from the reaction mixture, for example, as follows. After the solvent has, as necessary, been distilled off from the reaction mixture under a reduced pressure, the obtained residue is washed with a solvent such as ethyl acetate or hexane to give a crystalline phosphine compound (III). Where the phosphine compound (III) has a low solubility in the solvent, the reaction mixture is, without removal of the solvent by distillation, filtered to give the crystalline phosphine compound (III). The obtained phosphine compound (III) can be used for preparation of a telomerization catalyst as it is or, as necessary, after purification by recrystallization or like means.

The above reaction can suppress contamination of impurities into the phosphine compound (III), thus providing the phosphine compound (III) with high purity.

Next, the process for producing phosphine compounds (III) from alkali metal sulfonates (IV-2) is described.

The reaction of an alkali metal sulfonate (IV-2) and an amine (V) is carried out in the presence of at least one molar equivalent of water relative to the alkali metal sulfoante (IV-2). It is preferable to use the alkali metal sulfoante (IV-2) as its hydrate.

The reaction is carried out in the presence or absence of a solvent. Where the alkali metal sulfonate (IV-2) used is soluble in the amine (V), use of a solvent is not always necessary. However, where the sulfonate is hardly soluble or insoluble in the amine (V), it is desirable, in order to increase the reaction rate, to carry out the reaction in the presence of a solvent. The solvents that can dissolve both the alkali metal sulfonate (IV-2) and the amine (V) are preferred. Examples of usable solvents are alcohols, e.g. methanol, ethanol, 1-propanol, 2-propanol, 1-butanol, 2-butanol, 2-methyl-1-propanol and 2-methyl-2-propanol; ketones, e.g. acetone, 2-butanone, 3-methyl-2-butanone and 4-methyl-2-pentanone; ethers, e.g. diethyl ether, tetraethyleneglycol dimethyl ether, tetrahydrofuran and dioxane; and water. These solvents may be used either singly or in combination of 2 or more. Of these solvents, ethanol, 2-propanol or mixtures thereof is preferably used. The amount of the solvent used is not particularly limited, but it is desirably in a range of 0.5 to 100 ml based on 1 g of the alkali metal sulfonate (IV-2) used, more preferably in a range of 1 to 10 ml on the same basis, because too much amount impairs economical efficiency.

With the above reaction, the amine (V) is used desirably in an amount of 1.0 to 10.0 moles based on one mole of the alkali metal sulfonate (IV-2), more preferably in an amount of 1.0 to 5.0 moles on the same basic.

The reaction is carried out in the presence of carbon dioxide. If, instead of carbon dioxide, a mineral acid such as sulfuric acid or hydrochloric acid is used, the reaction mixture will contain the amine salt of the mineral acid and thus become of low purity.

Gaseous carbon dioxide or dry ice can be used as the carbon dioxide. Or, hydrogencarbonates or carbonates can be used to generate carbon dioxide in the reaction zone. The reaction pressure is desirably in a range of 0 to 0.98 MPa (atmospheric pressure to 10 kg/cm$^2$) (gauge pressure), more preferably in a range of 0 to 0.49 MPa (atmospheric pressure to 5 kg/cm$^2$) (gauge pressure). Unnecessarily high pressure will impair the economical efficiency. The reaction temperature is desirably in a range of 0 to 120° C., more preferably in a range of 50 to 90° C. The reaction time is, not particularly limited though, desirably in a range of 1 to 20 hours.

The thus obtained phosphine compound (III) can be separated from the reaction mixture, for example, as follows. The reaction mixture contains precipitates of a byproduct of an alkali metal hydrogencarbonate or carbonate. At first, the precipitates are removed by filtration, centrifugal separation or like means. Then, the solvent is distilled off from the reaction mixture under a reduced pressure, to yield the desired phosphine compound (III). The obtained phosphine compound (III) can, as necessary, be purified by recrystallization.

The sulfonic acids (IV-1) and alkali metal sulfonates (IV-2) can be derived by any known process from the corresponding phosphorus compounds represented by the general formula (VI) (hereinafter referred to as "phosphorus compounds (VI)")

(VI)

wherein R$^1$, R$^2$ and R$^3$ are as defined above. In order to obtain a high-purity phosphine compound (III), it is desirable to use the corresponding phosphorus compound (VI) with high purity. Although sulfonation of a phosphorus compound (VI) with fuming sulfuric acid will give the corresponding sulfonic acid (IV-1) in short steps and readily, this process generally produces relatively large amounts of impurities such as disulfonated products and oxidized products. It is therefore recommended to at first convert a sulfonic acid (IV-1) into an alkali metal sulfonate (IV-2) and, after removing the above impurities, to convert the alkali metal salt into the sulfonic acid (IV-1) by acid treatment or like means.

Examples of the phosphorus compounds (VI) are triphenylphosphine, tri(tolyl)phosphine, tri(ethylphenyl)phosphine, tri(propylphenyl)phosphine, tolyldiphenylphosphine, di(tolyl)phenylphosphine, di(ethylphenyl)phenylphosphine, tolyl(dimethylphenyl)phosphine, tris(trimethylphenyl)phosphine and tris(tetramethylphenyl)phosphine.

According to the present invention, there are provided telomerization catalysts (I) which, on telomerizing a conjugated diene and an active hydrogen compound continuously over a long period of time and on a commercial scale, causes no precipitation of inorganic salts and the like, and phosphonium salts (I) constituting the telomerization catalyst (I) and processes for producing the same. Use of these telomerization catalysts ensures production of alkadienyl compounds from conjugated dienes and active hydrogen compounds at high reaction rates and high selectivities, while causing no precipitation of catalyst components or inorganic salts or the like originating therefrom. The present invention also provides high-purity phosphine compounds (III) that give the phosphonium salts (I), as well as processes for producing in a simple manner the phosphine compounds (III) with high purity.

A further understanding of this invention can be obtained by reference to specific examples which are provided hereinbelow for purposes of illustration only and are not intended to be limitative of this invention.

EXAMPLE 1

Synthesis of triethylammonium 3-(diphenylphosphino)benzenesulfonate

1. Synthesis of sodium 3-(diphenylphosphino)benzenesulfonate

A 300-ml three-necked flask equipped with a thermometer, stirrer, dropping funnel and nitrogen inlet and outlet lines was charged with 110 g (1.12 moles) of concentrated sulfuric acid and 60 g (0.23 mole) of triphenylphosphine, and the air in the flask was replaced with nitrogen. To the contents with stirring 220 g of fuming sulfuric acid (content of sulfur trioxide: 25% by weight; moles of sulfur trioxide: 0.69 mole) was added dropwise over 1 hour, while the inside temperature was maintained at 25° C. After completion of the dropping, stirring was continued for 12 hours at an inside temperature of 25° C. The reaction mixture obtained was added dropwise onto 1.8 kg of ice water under an atmosphere of nitrogen and hydrolyzed and diluted. To the obtained aqueous solution, 1.5 liters of 4-methyl-2-pentanone was added at a room temperature and sufficiently mixed. After the mixture had been allowed to stand still, the 4-methyl-2-pentanone layer was separated. To the 4-methyl-2-pentanone layer thus obtained, 120 ml of a 5% by weight aqueous sodium hydroxide solution was added dropwise under an atmosphere of nitrogen, while the inside temperature was maintained at 25° C., to neutralize it. The aqueous layer was taken out from the reaction mixture, washed with 100 ml of 4-methyl-2-pentanone and again taken out by separation. The layer was condensed at 80° C. to a volume of 80 ml and then allowed to cool, to precipitate crystals. The crystals precipitated were separated by filtration and vacuum-dried at 60° C., 0.67 kPa (5 mmHg) for 2 hours, to yield 35 g of a white crystalline sodium 3-(diphenylphosphino)benzenesulfonate dihydrate.

2. Synthesis of triethylammonium 3-(diphenylphosphino)benzenesulfonate

A 300-ml three-necked flask equipped with a thermometer, stirrer, dropping funnel and nitrogen inlet and outlet lines was charged with 30 g (75 millimoles) of sodium 3-(diphenylphosphino)benzenesulfonate 2H$_2$O and 75 ml of water, and the air in the flask was replaced with nitrogen. To the contents with stirring 38 ml of 50% by weight sulfuric acid was added dropwise, while the inside temperature was maintained at 25° C. After completion of the dropping, stirring was continued for 1 hour at an inside temperature of 25° C. The reaction mixture obtained was mixed with 130 ml of 4-methyl-2-pentanone under an atmosphere of nitrogen and, after the mixture had been allowed to stand still, the 4-methyl-2-pentanone layer was separated. To the 4-methyl-2-pentanone layer thus obtained, 8.3 g (82 millimoles) of triethylamine was added dropwise under an atmosphere of nitrogen, while the inside temperature was maintained at 25° C., to neutralize it. The reaction mixture was condensed at 40 and 4.0 kPa (30 mmHg) to a volume of 70 ml, to form precipitates. The precipitates were separated by filtration and vacuum-dried, to give 31.6 g (yield: 95%) of a white powder. The powder was analyzed by high-performance liquid chromatography [eluent: a 35/65 by volume 0.01 mole/liter aqueous phosphoric acid solution/methanol; column: L-column ODS (4.6×150 mm, available from Chemicals Evaluation and Research Institute, Japan), and found to contain 0.8 mole % of the corresponding phosphine oxide. $^1$H-NMR spectrometry and $^{31}$P-NMR spectrometry of the white powder and atomic absorption analysis for the Na content revealed that it was triethylammonium 3-(diphenylphosphino)benzenesulfonate of the formula (VII). Iodometry of this powder showed that it had a purity of 98.5%.

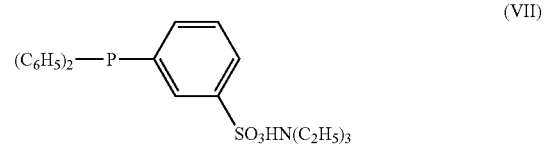

(VII)

$^1$H-NMR (270 MHz, CD$_3$OD, standard: TMS, ppm): δ 1.27 (t, J=7 Hz, 9H), 3.16 (q, 6H), 7.25–7.84 (m, 14H) $^{31}$P-NMR (D$_2$O, standard: 85% phosphoric acid, ppm): δ:−5.2

Atomic absorption analysis: Na undetected.

EXAMPLE 2

Synthesis of triethylammonium 3-(diphenylphosphino)benzenesulfonate

A 300-ml three-necked flask equipped with a thermometer, stirrer, dropping funnel and nitrogen inlet and outlet lines was charged with 110 g (1.12 moles) of concentrated sulfuric acid and 60 g (0.23 mole) of triphenylphosphine, and the air in the flask was replaced with nitrogen. To the contents with stirring 220 g of fuming sulfuric acid (content of sulfur trioxide: 25% by weight; moles of sulfur trioxide: 0.69 mole) was added dropwise over 1 hour, while the inside temperature was maintained at 25° C. After completion of the dropping, stirring was continued for 12 hours at an inside temperature of 25° C. The reaction mixture obtained was added dropwise onto 1.8 kg of ice water under an atmosphere of nitrogen and hydrolyzed and diluted. To the obtained aqueous solution, 1.5 liters of 4-methyl-2-pentanone was added at a room temperature and sufficiently mixed. After the mixture had been allowed to stand still, the 4-methyl-2-pentanone layer was separated. To the 4-methyl-2-pentanone layer thus obtained, 30 ml of triethylamine was added dropwise under an atmosphere of nitrogen, while the inside temperature was maintained at 25° C., to neutralize it. The reaction mixture obtained was condensed to a weight of about 250 g, which was then extracted with 200 ml of water. The water was distilled off under a reduced pressure and 47 g of a white solid was obtained. The white solid was found by analysis to be triethylammonium 3-(diphenylphosphino)benzenesulfonate (content of phosphine oxide: 5 mole %) having a purity of 90%.

EXAMPLE 3

Synthesis of triethylammonium 3-(diphenylphosphino)benzenesulfonate

A 60-ml pressure-proof glass vessel was charged with 4 g of the sodium 3-(diphenylphosphino)benzenesulfonate dihydrate obtained in the same manner as in Example 1, 4 g (40 millimoles) of triethylamine and 20 ml of a 1/1 by volume mixed liquid of ethanol and 2-propanol, and the air in the vessel was replaced with carbon dioxide. The inside pressure was set at 0.29 MPa by carbon dioxide, and the contents were stirred for 10 hours at an inside temperature of 80°. After completion of the reaction, the precipitates that formed were removed by filtration, and the filtrate was distilled off under a reduced pressure, to give precipitates of a white solid. The obtained solid was vacuum-dried to give 4.36 g (yield: 98%) of a white powder. The powder was analyzed by high-performance liquid chromatography [as in Example 1], and found to contain 0.2 mole % of the corresponding phosphine oxide. $^1$H-NMR spectrometry and $^{31}$P-NMR spectrometry of the white powder revealed that it was triethylammonium 3-(diphenylphosphino)benzenesulfonate.

COMPARATIVE EXAMPLE 1

Synthesis of triethylammonium 3-(diphenylphosphino)benzenesulfonate

A 100-ml three-necked flask equipped with a thermometer, stirrer, dropping funnel and nitrogen inlet and outlet lines was charged with 10 g (25 millimoles) of sodium 3-(diphenylphosphino)benzenesulfonate dihydrate and 20 ml of methanol and, after the air in the flask had been replaced with nitrogen, the flask was ice-cooled. To the contents with stirring 2.84 g (29 millimoles) of concentrated sulfuric acid was added dropwise, while the inside temperature was maintained at 8° C. or below. After completion of the dropping, 7.26 g (72 millimoles) of triethylamine was added dropwise under an atmosphere of nitrogen, while the inside temperature was maintained at 16° C. or below. The reaction mixture obtained was stirred for 1 hour at a room temperature and under an atmosphere of nitrogen, to give precipitates. The inorganic salt that precipitated was separated by filtration by means of suction. The filtrate was condensed under reduced pressure. To the condensed liquid 40 ml of ethyl acetate was added, to obtain a white solid. The solid was separated by filtration by means of suction and vacuum-dried, to give 10.96 g of a white powder. The powder was analyzed by high-performance liquid chromatography [as in Example 1] and found to contain 1.2 mole % of the corresponding phosphine oxide. $^1$H-NMR spectrometry of the white powder revealed that it was a mixture of triethylammonium 3-(diphenylphosphino)benzenesulfonate and salts of sulfuric acid and triethylamine, containing about 90% of the former. This results indicates that at least 10% of the sulfuric acid used for the reaction remained as the salt with triethylamine in the desired product. The white powder was further purified by recrystallization from a mixed solvent of ethyl acetate and 2-propanol, but the obtained product had a purity of only 94%.

EXAMPLE 4

Synthesis of a Phosphonium Salt

A 100-ml stainless steel autoclave equipped with a stirrer was charged with 0.048 g (0.214 millimole) of palladium acetate, 20 g (45 millimoles) of triethylammonium 3-(diphenylphosphino)benzenesulfonate, 15 g of water, 14 g of 2,7-octadien-1-ol and 55 ml of 1,4-dioxane, and the air in the autoclave was replaced by carbon dioxide. A pressure of 0.69 MPa (7 kg/cm²) (gauge pressure) was applied and the temperature was elevated to 80° C. The contents were heated and stirred for 13 hours, and then cooled. The reaction mixture was taken out and the solvent was removed by evaporation. The solid that precipitated was washed with diethyl ether and dried, to give 11 g of a white powder. The white powder was analyzed by high-performance liquid chromatography [as in Example 1], and showed no peak at the position of the starting material phosphine compound.

$^1$H-NMR spectrometry of the white powder revealed that it was a phosphonium salt of the formula (VIII).

$^1$H-NMR (270 MHz, CD$_3$OD, standard: TMS, ppm): δ 1.27–1.36 (m, 2H), 1.80–1.90 (m, 2H), 1.95–2.08 (m, 2H), 4.30 (dd, J=6.9 and 15 Hz, 2H), 4.88–4.98 (m, 2H), 5.31–5.48 (m, 1H), 5.64–5.90 (m, 2H), 7.20–7.90 (m, 12H), 8.10–8.30 (m, 2H)

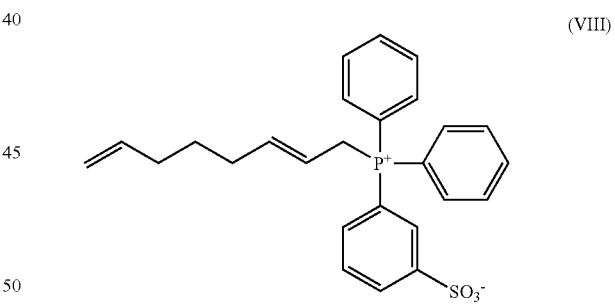

(VIII)

EXAMPLE 5

The telomerization of butadiene and water was carried out by the following process.

A 1-liter glass autoclave was charged with 123.8 g of water, 121.7 g of sulfolane, 41.2 g of triethylamine, 0.128 g of palladium acetate and 6.4 g of the phosphonium salt obtained in Example 4, and the air in the autoclave was replaced by carbon dioxide. The inside was pressurized by carbon dioxide to a pressure of 0.39 MPa (4 kg/cm²) (gauge pressure). The temperature was elevated to 70° C. and then 75 ml of 1,3-butadiene was introduced into the glass autoclave and the inside pressure was adjusted by carbon dioxide at 1.37 MPa (14 kg/cm²) (gauge pressure), to initiate reaction. After 30 minutes, 45 ml of 1,3-butadiene was further added. One hour after the start, the reaction was terminated. The reaction mixture was extracted with 450 ml of hexane. The hexane layer constituting the upper layer was taken out and analyzed. The catalyst liquid layer constituting the lower layer was returned to the reactor. The reaction was repeated 4 times. The results of analysis on the upper layer is shown in Table 1. It is clear from Table 1 that the catalyst suffered no deactivation and the telomerization reaction was successfully repeated.

TABLE 1

| Times repeated | 1 | 2 | 3 | 4 |
|---|---|---|---|---|
| 2,7-octadien-1-ol (millimoles) | 34 | 74 | 87 | 91 |
| 1,7-octadien-3-ol (millimoles) | 1.5 | 2.8 | 3.4 | 3.9 |

EXAMPLE 6

Preparation of Catalyst Liquid

A 100-ml stainless steel autoclave equipped with a stirrer was charged with 0.068 g (0.304 millimole) of palladium acetate, 2.7 g (6.08 millimoles) of triethylammonium 3-(diphenylphosphino)benzenesulfonate, 16 g of water, 4.28 g (34 millimoles) of 2,7-octadien-1-ol, 5.51 g (54.6 millimoles) of triethylamine and 17.1 g of sulfolane, and the air in the autoclave was replaced by carbon dioxide. The inside was pressurized by carbon dioxide to a pressure of 0.69 MPa (7 kg/cm²) (gauge pressure). The temperature was elevated to 80° C. The contents were heated with stirring under the same conditions for 13 hours and then cooled, to give a catalyst liquid. The catalyst liquid was analyzed by high-performance liquid chromatography [as in Example 1], which revealed that the triethylammonium 3-(diphenylphosphino)benzenesulfonate had totally been converted into the corresponding phosphonium salt.

EXAMPLE 7

The telomerization of butadiene and water was carried out continuously by the following process.

To a reactor, 1,3-butadine, water, sulfolane, triethylamine and the catalyst liquid obtained in Example 6 were continuously fed in such amounts as to constitute the following composition. The reaction was carried out under a carbon dioxide pressure of 1.37 MPa (14 kg/cm²) (gauge pressure) and at a temperature of 72° C. and at a residence time of 1 hour.

| | |
|---|---|
| 1,3-Butadiene | 6% by weight |
| Water | 24% by weight |
| Sulfolane | 40% by weight |
| Triethylamine | 7% by weight |
| Palladium | 200 ppm |

Phosphonium salt: 20 moles based on mole of palladium

The above reaction was continuously carried out for 3 months, during which no precipitation of solid such as inorganic salts was observed.

COMPARATIVE EXAMPLE 2

Example 6 was repeated except that lithim 3-(diphenylphosphino)benzenesulfonate was used instead of triethylammonium 3-(diphenylphosphino)benzenesulfonate, to prepare a catalyst liquid. The catalyst liquid was analyzed by high-performance liquid chromatography [as in Example 1], to be found that the lithim 3-(diphenylphosphino)benzenesulfonate had totally been converted into the corresponding phosphonium salt. Next, Example 7 was repeated except that this catalyst liquid was continuously fed instead of the catalyst liquid obtained in Example 6, to carry out a similar reaction continuously for 3 months. During the reaction, there was observed formation of precipitates of lithium carbonate and/or lithium hydrogencarbonate.

Obviously, numerous modifications and variations of the present invention are possible in light of the above teachings. It is therefore to be understood that within the scope of the appended claims, the invention may be practiced otherwise than as specifically described herein.

What is claimed is:

1. A telomerization catalyst comprising a phosphonium salt represented by the formula (I)

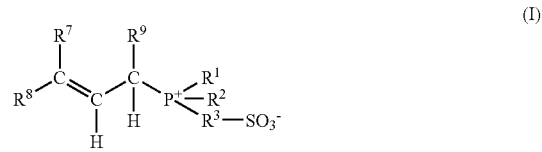

wherein $R^1$ and $R^2$ each independently represents a phenyl group which may be substituted by a lower alkyl group, $R^3$ represents a phenylene group which may be substituted by a lower alkyl group, $R^7$ and $R^8$ each independently represents a hydrogen atom or a hydrocarbon group having 1 to 12 carbon atoms which may be substituted and $R^9$ represents a hydrogen atom or a hydrocarbon group having 1 to 5 carbon atoms which may be substituted; and a palladium compound but comprising no alkali metal compound.

2. The telomerization catalyst according to claim 1, wherein in the formula (I) $R^7$ and $R^8$ each independently represents a hydrogen atom or an aliphatic hydrocarbon group having 1 to 12 carbon atoms and $R^9$ represents a hydrogen atom or an aliphatic hydrocarbon group having 1 to 5 carbon atoms.

3. The telomerization catalyst according to claim 1, wherein in the formula (I) $R^1$ and $R^2$ each independently represents a phenyl group or a phenyl group having a methyl group or ethyl group, and $R^3$ represents a 1,3-phenylene group or a 1,3-phenylene group having a methyl group or ethyl group.

4. The telomerization catalyst according to claim 1, wherein in the formula (I) $R^1$ and $R^2$ each independently represents a phenyl group or a 2-methylphenyl group, and $R^3$ represents a 1,3-phenylene group or a 4-methyl-1,3-phenylene group.

5. The telomerization catalyst according to claim 1, wherein the concentration of said phosphonium salt is at least 2 moles per gram-atom of palladium contained in said palladium compound.

6. The telomerization catalyst according to claim 5, wherein the concentration of said phosphonium salt is in a range of 4 to 50 moles per gram-atom of palladium contained in said palladium compound.

7. A process for producing an alkadienyl compound, which comprises reacting a conjugated diene with an active hydrogen compound in the presence of a telomerization catalyst, wherein said telomerization catalyst comprises a phosphonium salt represented by the formula (I)

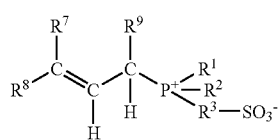

wherein $R^1$ and R2 each independently represents a phenyl group which may be independently substituted by a lower alkyl group, $R^3$ represents a phenylene group which may be substituted by a lower alkyl group, $R^7$ and $R^8$ each independently represents a hydrogen atom or a hydrocarbon group having 1 to 12 carbon atoms which may be substituted and $R^9$ represents a hydrogen atom or a hydrocarbon group having 1 to 5 carbon atoms which may be substituted, and a palladium compound but comprising no alkali metal compound.

8. The process according to claim 7, wherein in the formula (I) $R^7$ and $R^8$ each independently represents a hydrogen atom or an aliphatic hydrocarbon group having 1 to 12 carbon atoms and $R^9$ represents a hydrogen atom or an aliphatic hydrocarbon group having 1 to 5 carbon atoms.

9. The process according to claim 7, wherein in the formula (I) $R^1$ and $R^2$ each independently represents a phenyl group or a phenylene group having a methyl group or ethyl group, and $R^3$ represents a 1,3-phenylene group or a 1,3-phenylene group having a methyl group or ethyl group.

10. The process according to claim 9, wherein in the formula (I) $R^1$ and $R^2$ each independently represents a phenyl group or a 2-methylphenyl group, and $R^3$ represents a 1,3-phenylene group or a 4-methyl-1,3-phenylene group.

11. The process according to claim 7, wherein the concentration of said phosphonium salt is at least 2 moles per gram-atom of palladium contained in said palladium compound.

12. The process according to claim 11, wherein the concentration of said phosphonium salt is in a range of 4 to 50 moles per gram-atom of palladium contained in said palladium compound.

13. The process according to claim 7, wherein the reaction temperature is in a range of 40 to 100° C.

14. The process according to claim 7, wherein said active hydrogen compound is water, an alcohol or a carboxylic acid.

* * * * *